(12) United States Patent
Yu et al.

(10) Patent No.: US 10,482,215 B2
(45) Date of Patent: Nov. 19, 2019

(54) UNIFIED COMPUTATIONAL METHOD AND SYSTEM FOR PATIENT-SPECIFIC HEMODYNAMICS

(71) Applicants: Indiana University Research and Technology Corporation, Indianapolis, IN (US); Kent State University, Kent, OH (US)

(72) Inventors: Huidan Yu, Indianapolis, IN (US); Chen Lin, Carmel, IN (US); Ye Zhao, Orange, OH (US)

(73) Assignees: Indiana University Research and Technology Corporation, Indianapolis, IN (US); Kent State University, Kent, OH (US)

( * ) Notice: Subject to any disclaimer, the term of this patent is extended or adjusted under 35 U.S.C. 154(b) by 0 days.

(21) Appl. No.: 15/520,283

(22) PCT Filed: Oct. 22, 2015

(86) PCT No.: PCT/US2015/056942
§ 371 (c)(1),
(2) Date: Apr. 19, 2017

(87) PCT Pub. No.: WO2016/065161
PCT Pub. Date: Apr. 28, 2016

(65) Prior Publication Data
US 2017/0337327 A1 Nov. 23, 2017

Related U.S. Application Data

(60) Provisional application No. 62/066,993, filed on Oct. 22, 2014.

(51) Int. Cl.
*G06F 19/00* (2018.01)
*G06T 7/00* (2017.01)
(Continued)

(52) U.S. Cl.
CPC ......... *G06F 19/321* (2013.01); *G06K 9/4604* (2013.01); *G06T 7/0012* (2013.01);
(Continued)

(58) Field of Classification Search
None
See application file for complete search history.

(56) References Cited

U.S. PATENT DOCUMENTS

| | | | |
|---|---|---|---|
| 6,516,080 B1 | 2/2003 | Nur | |
| 8,356,714 B2 * | 1/2013 | Sulchek | B01D 45/14 209/132 |

(Continued)

FOREIGN PATENT DOCUMENTS

| | | | | |
|---|---|---|---|---|
| DE | 102005035181 | * | 3/2006 | ............. G06T 13/60 |
| DE | 102005035181 B4 | * | 6/2006 | ............. G06T 13/60 |
| WO | WO2006010609 A2 | | 2/2006 | |

OTHER PUBLICATIONS

Machine Translation DE 102005035181 A1 (Year: 2006).*

(Continued)

*Primary Examiner* — Michelle M Entezari
(74) *Attorney, Agent, or Firm* — Faegre Baker Daniels LLP (57) ABSTRACT

A method for computing patient-specific hemodynamics. The method includes receiving three dimensional imaging data of a patent, extracting anatomical data from the three dimensional imaging data, calculating velocity and pressure fields corresponding to the extracted anatomical data, and calculating displacement and velocity of extracted solid particles corresponding to the anatomical data. The anatomical data comprises an anatomical boundary.

12 Claims, 7 Drawing Sheets

(51) Int. Cl.

| | |
|---|---|
| *G06T 7/12* | (2017.01) |
| *G06T 7/11* | (2017.01) |
| *G06K 9/46* | (2006.01) |
| *G16H 50/50* | (2018.01) |
| *A61B 6/03* | (2006.01) |
| *A61B 6/00* | (2006.01) |
| *A61B 5/00* | (2006.01) |
| *A61B 8/06* | (2006.01) |
| *A61B 8/08* | (2006.01) |
| *G06F 17/11* | (2006.01) |

(52) U.S. Cl.
CPC .............. *G06T 7/11* (2017.01); *G06T 7/12* (2017.01); *A61B 5/0033* (2013.01); *A61B 6/032* (2013.01); *A61B 6/507* (2013.01); *A61B 6/5217* (2013.01); *A61B 8/06* (2013.01); *A61B 8/488* (2013.01); *A61B 8/5223* (2013.01); *A61B 2576/02* (2013.01); *G06F 17/11* (2013.01); *G06T 2200/28* (2013.01); *G06T 2207/10028* (2013.01); *G06T 2207/10072* (2013.01); *G06T 2207/10081* (2013.01); *G06T 2207/10088* (2013.01); *G06T 2207/10136* (2013.01); *G06T 2207/20161* (2013.01); *G06T 2207/30104* (2013.01); *G16H 50/50* (2018.01)

(56) References Cited

U.S. PATENT DOCUMENTS

| | | | |
|---|---|---|---|
| 8,812,246 B2 | 8/2014 | Taylor | |
| 8,831,320 B2* | 9/2014 | Bernhardt | A61B 6/03 382/131 |
| 9,031,819 B2* | 5/2015 | Chen | G06F 17/5018 703/9 |
| 2012/0072190 A1 | 3/2012 | Sharma et al. | |
| 2014/0249790 A1 | 9/2014 | Spilker et al. | |
| 2014/0294137 A1 | 10/2014 | Bernhardt et al. | |

OTHER PUBLICATIONS

Zhang R, Chen H, Qian YH, Chen S. Effective volumetric lattice Boltzmann scheme. Physical review E. Apr. 24, 2001;63(5):056705. (Year: 2001).*

Wu TH, Qi D. Lattice-Boltzmann lattice-spring simulations of influence of deformable blockages on blood fluids in an elastic vessel. Computers & Fluids. Sep. 20, 2017;155:103-11. (Year: 2017).*

Tian FB, Luo H, Zhu L, Liao JC, Lu XY. An efficient immersed boundary-lattice Boltzmann method for the hydrodynamic interaction of elastic filaments. Journal of computational physics. Aug. 10, 2011;230(19):7266-83. (Year: 2011).*

Wu, T.H. And Qi, D., 2017. Lattice-Boltzmann lattice-spring simulations of influence of deformable blockages on blood fluids in an elastic vessel. Computers & Fluids, 155, pp. 103-111. (Year: 2017).*

Frantziskonis, George N. "Lattice Boltzmann method for multimode wave propagation in viscoelastic media and in elastic solids." Physical Review E 83, No. 6 (2011): 066703. (Year: 2011).*

Buxton, Gavin A., Rolf Verberg, David Jasnow, and Anna C. Balazs. "Newtonian fluid meets an elastic solid: coupling lattice Boltzmann and lattice-spring models." Physical Review E 71, No. 5 (2005): 056707. (Year: 2005).*

Navidbakhsh, M., and M. Rezazadeh. "An immersed boundary-lattice Boltzmann model for simulation of malaria-infected red blood cell in micro-channel." Scientia Iranica 19.5 (2012): 1329-1336. (Year: 2012).*

International Search Report and Written Opinion issued by the ISA/US, Commissioner for Patents, dated Jan. 11, 2016, for International Application No. PCT/US2015/056942; 6 pages.

Lattice Boltzmann Methods, National Institute of Standards and Technology (NIST), Retrieved Dec. 8, 2015, Retrieved from the Internet <http://math.nist.gov/mcsd/savg/parallel/lb/>; 3 pages.

International Preliminary Report on Patentability issued by The International Bureau of WIPO, dated Apr. 25, 2017, for International Application No. PCT/US2015/056942; 5 pages.

Yu, H., Chen, X., Wang, Z., Deep, D., Lima, E. Zhao, Y. and Teague, D. S.: 'Mass-conserved volumetric lattice Boltzmann method for complex flows with willfully moving boundaries', Physical Review E, 2014, 89.

Yu, H.D., Wang, Z. Q., Chen, N., Zhao, Y., et al: 'Unified mesoscale modeling for patient-specific computational hemodynamics', Annals of Biomedical Engineering, 2014, pp. submitted.

Filippova, O., and Hanel, D.: 'A novel lattice BGK approach for low Mach No. combustion', Journal of Computational Physics, 2000, 158, (2), pp. 139-160.

He, X.Y., and Doolen, G.D.: 'Lattice Boltzmann method on a curvilinear coordinate system: Vortex shedding behind a circular cylinder', Physical Review E, 1997, 56, (1), pp. 434-440.

Mei, R.W., Luo, L.S., and Shyy, W.: 'An accurate curved boundary treatment in the lattice Boltzmann method', Journal of Computational Physics, 1999, 155, (2), pp. 307-330.

Yin, X.W., and Zhang, J.F.: 'An improved bounce-back scheme for complex boundary conditions in lattice Boltzmann method', Journal of Computational Physics, 2012, 231, (11), pp. 4295-4303.

Ladd, A.J.C.: Numerical Simulations of Particulate Suspensions via A Discretized Boltamann-equation—Part 1. Theoretical Foundations, Lawrence Livermore National Laboratory. Livermore, California, Jun. 25, 2993, pp. 1-36; Journal of Fluid Mechanics, 1994, 271, pp.311-339.

Ladd, A.J.C.: Numerical Simulations of Particulate Suspensions via A Discretized Boltamann Equation—Part II. Numerical Results. Lawrence Livermore National Laboratory. Livermore, California, Jun. 25, 2993, pp. 1-41; Journal of Fluid Mechanics, 1994, 271, pp. 285-309.

Bouzidi, M., Firdaouss, M., and Lallemand, P.: 'Momentum transfer of a Boltzmann-lattice fluid with boundries', Physics of Fluids, 2001, 13, (11), pp. 3452-3459.

Aidun, C.K., and Lu, Y.N.: 'Lattice Boltzmann Simulation of Solid Particles Suspended in Fluid', Journal of Statistical Physics, 1995, 81, (1-2), pp. 49-61.

Hirt, C.W.N., B.D.: 'Volume of fluid (VOF) method for the dynamics of free Boundires', Journal of Computational Physics, 1981, 39, (1), pp. 201-225.

Caselles, V., Kimmel, R., and Sapiro, G.: 'Geodesic Active Contours', Int'l J. Comp. Vision, 1997, 22, pp. 61-97.

Hagan, A.a.Z., Y.: 'Parallel 3D Image Segmentation of Large Data Sets on a GPU Cluster', in Editor (Ed.)/\(Eds.): 'Book Parallel 3D Image Segmentation of Large Data Sets on a GPU Cluster' (Springer, 2009, edn.), pp. 960-969.

Sun, X., Wang, Z., and Chen, G.: 'Parallel active contour with Lattice Boltzmann scheme on modern GPU', in Editor (Ed.)/\ (Eds.): 'Book Parallel active contour with Lattice Boltzmann scheme on modern GPU' (IEEE, 2012, edn.), pp. 1709-1712.

Wang, Z., Yan, Z., and Chen, G.: 'Lattice Boltzmann Method of Active Contour for Image Segmentation', pp. 338-343.

Buxton, G.A., Care, C.M., and Cleaver, D.J.: 'A lattice spring model of heterogeneous materials with plasticity', Modelling and Simulation in Materials Science and Engineering, 2001, 9, (6), pp. 485-497.

Hassold, G.N.a.S., D.J.: 'Brittle Fracture in Materials with Random Defects', Phys. Rev. B, 1989, 39.

Tuckerman, M., Berne, B.J., Martyna, G.J.: 'Reversible multiple time scale molecular-dynamics', J. Chem. Phys., 1992, 97.

Amenta, N.a.B., M.: 'Surface Reconstruction by Voronoi Filtering,' Discrete and Comput Geom., 1999, 22, pp. 481-504.

Zhao, H.-K., Osher, S., and Fedkiw, R.: 'Fast surface reconstruction using the level set method', in Editor (Ed.)/\(Eds.): 'Book Fast surface reconstruction using the level set method' (IEEE, 2001, edn.), pp. 194-201.

(56) References Cited

OTHER PUBLICATIONS

Enright, D., Fedkiw, R., Ferziger, J., and Mitchell, I.: 'A Hybrid Particle Level Set Method for Improved Interface Capturing', Journal of Computational Physics, 2002, 183, pp. 83-116.

* cited by examiner

UNIFIED COMPUTATIONAL METHOD AND SYSTEM FOR PATIENT-SPECIFIC HEMODYNAMICS

CROSS-REFERENCE TO RELATED APPLICATIONS

This application is a United States national stage application under 35 U.S.C. § 371 of International Patent Application No. PCT/US2015/056942, filed Oct. 22, 2015, which in turn claims priority to U.S. Provisional Application Ser. No. 62/066,993, filed on Oct. 22, 2014, the entire disclosures of which are both hereby expressly incorporated by reference.

FIELD OF THE DISCLOSURE

The present disclosure relates to a system for non-invasively quantifying in vivo blood flow and flow-artery interaction in humans and a computation methodology implement by the system for non-invasively quantifying the in vivo blood flow and flow-artery interaction in humans.

BACKGROUND OF THE DISCLOSURE

While imaging may accurately identify anatomic narrowing in an artery, it does not assess important underlying functional data, such as the fluid dynamics of blood and the dynamic interaction between the blood flow and artery/plaque wall because it is limited by relatively low resolution, lengthy data acquisition, and high expense. Computational fluid dynamics has become a unique and powerful research tool that is capable of noninvasively accessing in vivo blood flows and quantifying hemodynamics and fluid-structure interaction details in arteries. Recently, patient-specific computational hemodynamics, including reading 3-D image data from CT/MRI scanning, segmenting anatomical structures, generating meshes, and modeling blood flows, has emerged.

The highly nonlinear and multidisciplinary nature of the complex fluid-structure interaction problem poses formidable challenges in existing macroscopic computational methodologies of patient-specific computational hemodynamics.

First, most existing patient-specific computational hemodynamics research employs macroscopic Navier-Stokes solvers, either an in-house program or commercial computational fluid dynamics software, to solve the fluid dynamics. The interfacial dynamic behavior between blood flow and artery/plaque can only be modeled in very complicated ways. Meanwhile, macroscopic Navier-Stokes solvers are often computationally expensive because of the lack of suitability for efficient parallel acceleration.

Second, almost all the current patient-specific computational hemodynamics research relies on external image processing software to extract anatomical structures from CT/MRI imaging data. The computation efficiency is limited as most available software is not parallelized.

Third, data reconstruction and mesh generation are needed to fill the gap between image processing software and a computational fluid dynamics solver, when separately employed, which inevitably introduces extra time, conversion errors, and inaccuracy.

SUMMARY OF THE DISCLOSURE

In one embodiment, the present disclosure provides a method of non-invasively quantifying in vivo blood flow and flow-artery interaction in an artery, comprising receiving image data of anatomical features of the artery, processing the image data on a GPU parallel-computation framework employing mesoscale models, and displaying information representing the flow-artery interaction, wherein processing comprises using a simplified lattice Boltzmann method ("SLBM") to model anatomical segmentation of the artery, using a volumetric lattice Boltzmann method ("VLBM") to model fluid dynamics of the flow-artery interaction, using a lattice spring method ("LSM") to model structure mechanics of the flow-artery interaction, and using the SLBM to model interface tracking of the flow-artery interaction. In one aspect of this embodiment, receiving image data comprises receiving image data from at least one of a CT scanner, an MRI imager and an ultrasound Doppler imager. In another aspect, displaying information representing the flow-artery interaction comprises displaying at least one of a 3D blood flow velocity map and a wall shear stress map. In yet another aspect, the GPU parallel-computation framework is a GPU-equipped workstation. In still another aspect, using an SLBM includes performing a collision calculation, performing a streaming calculation and updating a distance function. In a variant of this aspect, performing a collision calculation comprises solving $f'_i(\vec{r},t) = f_i(\vec{r},t) - [f_i(\vec{r},t) - f_i^{eq}(\vec{r},t)]/\tau + F_i \Delta t$. In another variant of this aspect, performing a streaming calculation comprises solving $f_i(\vec{r} + \vec{e}_i \Delta t, t+\Delta t) = f'_i(\vec{r},t)$. In yet another variant, updating a distance function comprises calculating $\varphi = \Sigma_i f_i$. In another aspect of this embodiment, using a VLBM includes performing a collision calculation and performing a streaming calculation. In a variant of this aspect, performing a collision calculation comprises solving $n'_i(\vec{r},t) = n_i(\vec{r},t) - [n_i(\vec{r},t) - n_i^{eq}(\vec{r},t)]/\tau$. In another variant, performing a streaming calculation comprises solving $n_i(\vec{r}+\vec{e}_i \Delta t, t+\Delta t) = n'_i(\vec{r},t)$. In yet another variant, using a VLBM includes determining boundary induced fluid migration by solving $N = \Sigma_i n_i$, $N\vec{u} = \Sigma_i n_i \vec{e}_i$.

In another embodiment, the present disclosure provides a method for computing in vivo patient-specific hemodynamics noninvasively, comprising receiving three dimensional imaging data from an imaging source, extracting anatomical data from the three dimensional imaging data, the anatomical data comprising an anatomical boundary, calculating fluid dynamics and fluid structure interaction quantities including velocity and pressure fields, and wall shear stress corresponding to the extracted anatomical data, and displaying the fluid dynamics and fluid structure interaction quantities and wall shear stress. In one aspect of this embodiment, extracting anatomical data comprises calculating a distance function and a solid ratio of boundary cells. In another aspect, calculating fluid dynamics and fluid-structure interaction quantities comprises performing a VLBM for fluid dynamics, performing an LSM for structural mechanics, and coupling the VLBM and the LSM and updating the fluid dynamics and fluid structure interaction quantities. A variant of this aspect further comprises calculating a solid-volume ratio as a function of a portion of the updated fluid dynamics and fluid structure interaction quantities.

According to another embodiment, a system for computing in vivo patient-specific hemodynamics noninvasively is provided, comprising an imager configured for imaging a patient and providing three-dimensional imaging data of the patient, a GPU-equipped workstation configured to provide a parallelized implementation of a framework comprising a processor configured to receive the three-dimensional imaging data of the patient, extract anatomical data from the three-dimensional imaging data, the anatomical data comprising an anatomical boundary, calculate fluid dynamics and fluid structure interaction quantities including velocity, pressure, and wall shear stress distribution corresponding to the extracted anatomical data, and output a visualization of the fluid dynamics and wall shear stress distribution, and a visualization platform configured for receiving and displaying the visualization of the fluid dynamics and wall shear stress distribution. In one aspect of this embodiment the three-dimensional imaging data is data from at least one of a CT scanner, an MRI imager and an ultrasound Doppler imager. In another aspect, the processor is configured to extract anatomical data using an SLBM, execution of which includes performing a collision calculation, performing a streaming calculation and updating a distance function. In another aspect, the processor is configured to calculate fluid dynamics and fluid structure interaction quantities using a VLBM, execution of which includes performing a collision calculation and performing a streaming calculation.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION OF THE DISCLOSURE

Reference to the drawings illustrating various views of exemplary embodiments of the present disclosure is now made. In the drawings and the description of the drawings herein, certain terminology is used for convenience only and is not to be taken as limiting the embodiments of the present disclosure. Furthermore, in the drawings and the description below, like numerals indicate like elements throughout.

In accordance with an exemplary embodiment of the present disclosure, there is provided a computational method that non-invasively quantifies in vivo blood flow and flow-artery interaction in human arteries based on CT/MRI scanning together with ultrasound Doppler recording within clinically acceptable time. The exemplary method synergistically combines novel mesoscale modeling for image segmentation, fluid dynamics, structural mechanics, and interfacial tracking. In an exemplary embodiment of an implementation of the exemplary method, a graphics processing unit (GPU) is used to accelerate the computation through highly efficient parallelization for solving 3-D transitional fluid-structure interactions in biomechanical geometries, thereby providing computational advantages over existing parallel-inefficient macroscopic methodologies.

The exemplary method is implemented in a unified platform for segmentation, computational fluid dynamics, and fluid-structure interaction. The method implements all-mesoscale modeling, and because it is unified, there are no gaps among the models for anatomical extraction, fluid dynamics, solid mechanics, and interface tracking, thereby avoiding data reconstruction and mesh generation that existing methods include to their detriment. Implementation on a GPU platform in the exemplary embodiment provides for fast computation without requiring remote supercomputing.

The method enables massive secondary analysis of existing medical images via direct and parametric simulations taking advantage of the fast computation (e.g., within thirty minutes for one execution) to identify hemodynamic indicators through statistics for clinical assessment and prediction of fatal cardiovascular diseases such as stroke and heart attack. The method also facilitates access of medical practitioners to the quantitative flow information in diseased arteries simultaneously with CT/MRI imaging for lesion diagnosis and assessment.

Figure 1:
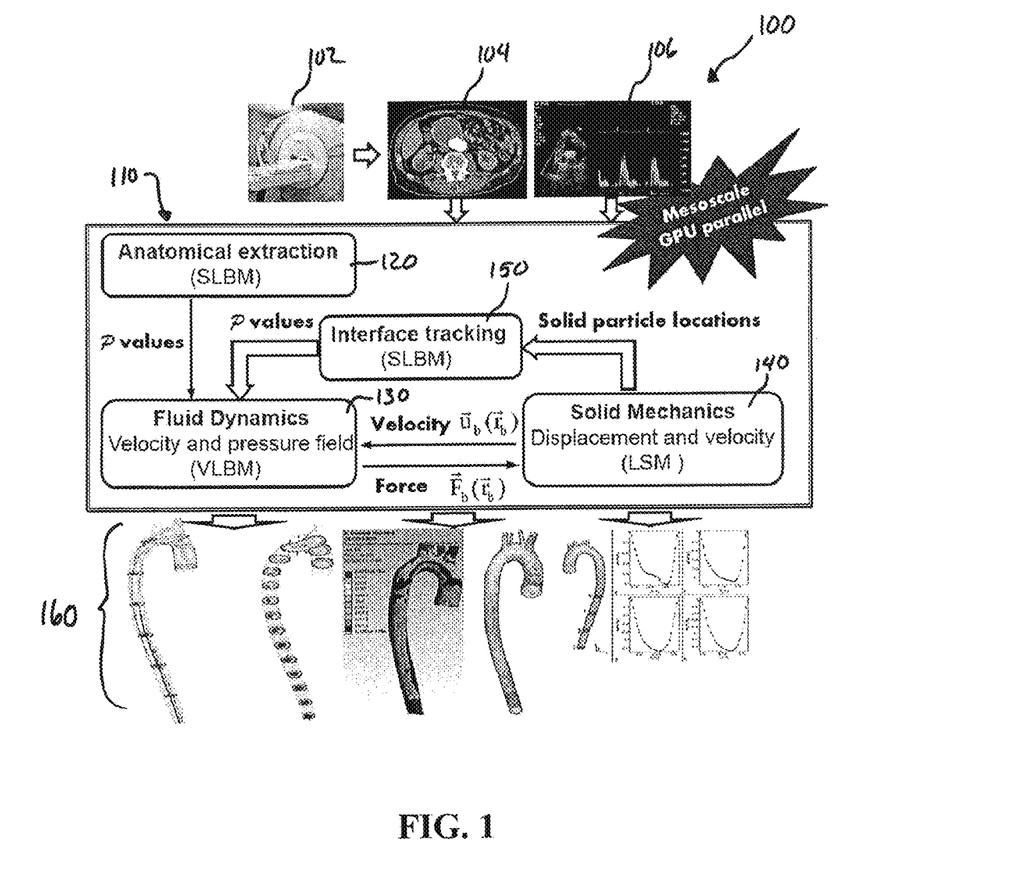
FIG. 1 is a flowchart illustrating a medical system architecture using a CT/MRI imager and/or ultrasound Doppler recordings to quantify in vivo blood flow and flow-artery interactions in human arteries, in accordance with an exemplary embodiment of the present disclosure.

Referring now to FIG. 1, there is illustrated a flowchart of a medical system architecture, generally designated as 100, for quantifying in vivo blood flow and flow-artery interactions in human arteries based on CT/MRI images 104 obtained from a CT scanner or MRI imager 102 or ultrasound Doppler recordings 106, in accordance with an exemplary embodiment of the present disclosure. The CT/MRI images 104 or ultrasound Doppler recordings 106 are processed in a GPU parallel-computation framework 110 employing mesoscale models or methods 120, 130, 140, and 150.

The framework 110 performs a simplified lattice Boltzmann method (SLBM) 120 for modeling anatomical segmentation, a volumetric lattice Boltzmann method (VLBM) 130 for modeling fluid dynamics, a lattice spring method (LSM) 140 for modeling structure mechanics, and a simplified lattice Boltzmann method (SLBM) 150 for modeling interface tracking. The framework 110 seamlessly integrates all of the mesoscale models 120, 130, 140, and 150 on a unified computing platform accelerated by a GPU, taking advantage of the inherent data locality of mesoscopic approaches, as discussed in more detail below. The framework 110 outputs the calculated in vivo fluid dynamics of blood and the dynamic interaction between the blood flow and the artery/plaque wall as results 160.

Figure 2:
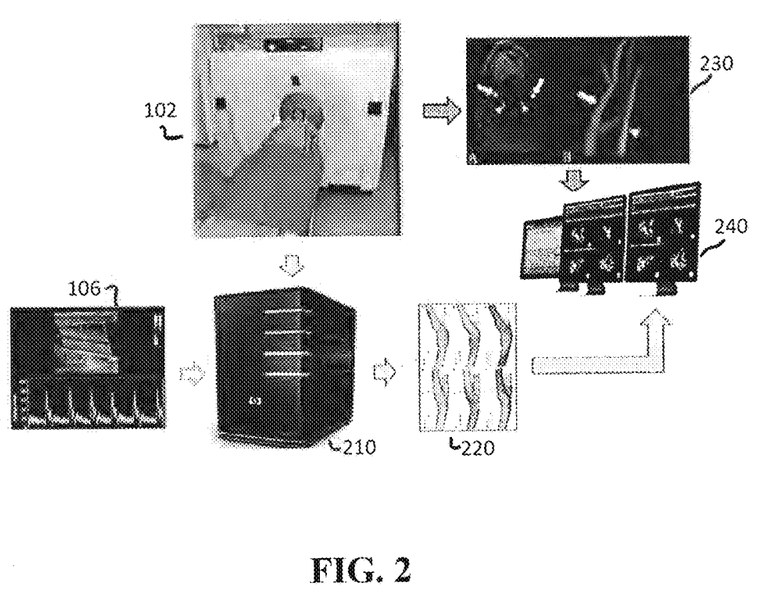
FIG. 2 illustrates a medical computing system for implementing the system architecture of FIG. 1, in accordance with an exemplary embodiment of the present disclosure.

Referring now to FIG. 2, there is illustrated a medical computing system, generally designated as 200, for implementing the system architecture 100, in accordance with an exemplary embodiment of the present disclosure. The medical system 200 comprises the CT scanner or MRI imager 102 and/or an ultrasound Doppler imager 106, or any combination of these imaging devices. The CT scanner/MRI imager 102 and/or ultrasound Doppler imager 106 are connected to a local GPU-equipped workstation 210 where unified computation for anatomical segmentation, computational fluid dynamics and fluid-structure interaction are unified modeled and computed. The results 220 generated by simulation such as 3D blood flow velocity (BFV) maps and wall shear stress (WSS) maps will be converted into standard DICOM images and sent to the appropriate visualization platforms 240 together with diagnostic images 230 from imager 102 as a comprehensive data set, accessible to both radiologists and referring physicians to aid the diagnosis and evaluation of vascular abnormalities.

The GPU-equipped workstation 210 is programmed with software instructions that when executed by the microprocessor of the workstation 210 implement the functionality of the framework 110 described herein. Accordingly, the software instructions provide for the workstation 210 receiving the CT/MRI images 104 and/or ultrasound Doppler images 106, and processing the received images using the framework 110. The GPU-equipped workstation 210 outputs the results (160 in FIG. 1 and 220 in FIG. 2), which are transmitted over a network (wired or wireless) to the appropriate visualization platforms 240 to be viewed by a medical doctor, nurse, or technician. The visualization platforms 240 are programmed with software instructions that when executed by the microprocessor of the visualization platforms 240 provide for displaying the results 160, 220 on the display of the visualization platforms 240.

In an exemplary embodiment of the system 200, the GPU-equipped workstation 210 implements the functionality of the framework 110 described herein. Accordingly, the software instructions executed by the workstation 210 cause the workstation 210 to receive the CT/MRI images 104 and/or ultrasound Doppler images from the CT scanner/MRI imager 102 and/or ultrasound Doppler imager 106, respectively, process the received images using the framework 110, and display the results 160, 220 on the visualization platforms 240 together with other imaging information 230.

Figure 3:
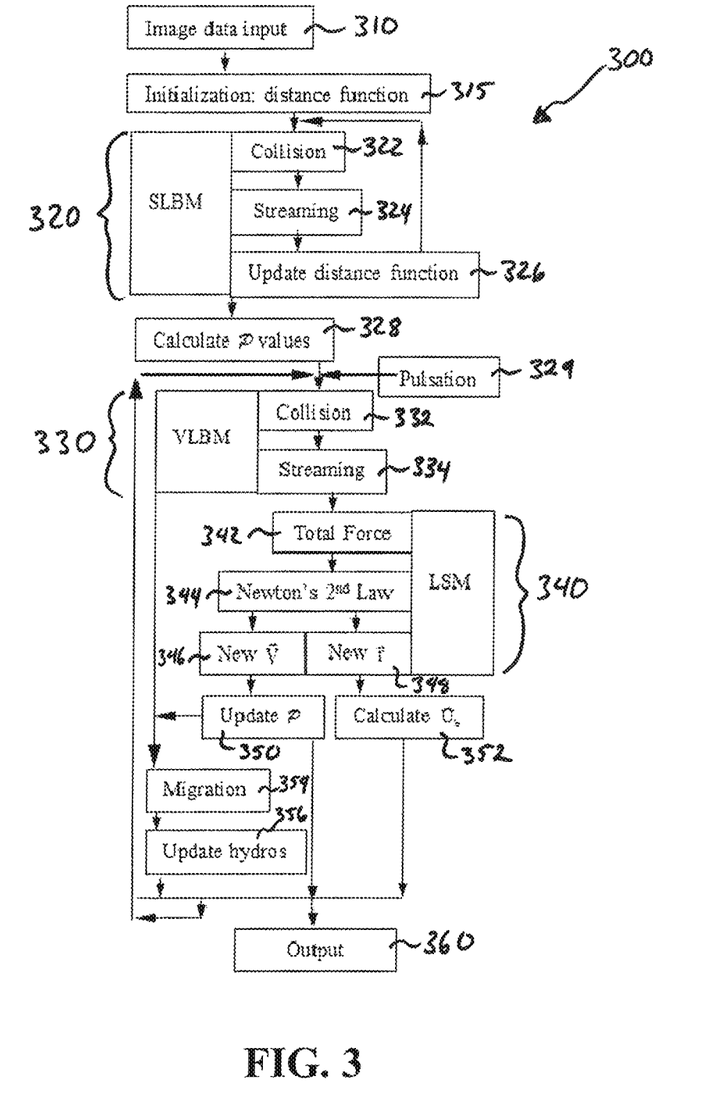
FIG. 3 is a flowchart for modeling together with an implementation sequence for quantifying in vivo blood flow and flow-artery interactions in human arteries, in accordance with an exemplary embodiment of the present disclosure.

Referring now to FIG. 3, there is illustrated an exemplary embodiment of a method, generally designated as 300, for quantifying in vivo blood flow and flow-artery interactions in human arteries. The method 300 is an exemplary implementation of the framework 110 and the methods 120, 130, 140, and 150 thereof and processes the CT/MRI images 104 and/or ultrasound Doppler recordings 106 to provide the results 160, 220. Subroutines 320, 330, and 340 of the method 300 correspond, respectively, to the methods 120/150, 130, and 140 of the framework 110.

The method 300 begins by receiving the CT/MRI images 104 and/or ultrasound Doppler images from the CT scanner/MRI imager 102 and/or ultrasound Doppler imager 106 at step 310. In step 315, a distance function is initialized.

The method 300 continues to the subroutine 320, which performs image segmentation or updates the interface between blood and artery/plaque wall, depending on when the subroutine 320 is accessed within the framework 110. Steps 322, 324, and 326 of collision, streaming, and updating the distance function are performed. After completing of the subroutine 320, step 328 of calculating P values and step 329 of pulsation are performed.

The method 300 continues to the subroutine 330 for extracting the anatomical segmentation. A step 332 of collision and a step 334 of streaming are performed. The method 300 then continues to the subroutine 340 for solving fluid dynamics and fluid-structure interaction. Steps 342, 344, 346, and 348 of calculating total force, Newton's Second Law, new $\vec{V}$, and new $\vec{r}$, are respectively performed. P is then updated at step 350, and U is calculated at step 352.

Finally, the method 300 continues to a step 354 of migration, and a step 356 of updating hydrodynamic variables. The method 300 provides the updated hydrodynamic variables from step 356 and the updated P from the step 350 to the subroutine 330. The method loops through the subroutines 330 and 340 and once complete provides the results 160, 220 in a step 360 of outputting the results 160.

Simplified Lattice Boltzmann Method

Figure 8:
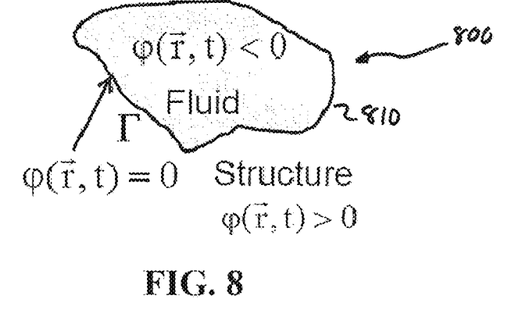
FIG. 8 illustrates a distance function, in accordance with an exemplary embodiment of the present disclosure.

Geometric active contour has been a popular technique for image segmentation to extract object boundaries from medical images. Given a 3D medical imaging dataset 104 or 106 from the CT scanner/MRI imager 102, the anatomical structures can be implicitly achieved by tracking a level set function ($\varphi(\vec{r}, t)$, shown in FIG. 8), which is defined over an evolving distance field in the whole domain 800. Given an interface, Γ, 810, negative, zero, and positive signs correspond to inside of, at, and outside of the fluid domain 800. The level set starts from an initial seeding contour, evolves following a partial differential equation, $$\frac{\partial \varphi}{\partial t} = \nabla(g\nabla\varphi) + \beta\varphi, \quad (1.)$$

and converges at the boundaries of arteries/plaques. The level set partial differential equation (1) can be considered as comprising a nonlinear diffusion equation with an external driving function.

The framework 110 and the method 300 solve partial differential equation (1) by the SLBM 120, in accordance with an exemplary embodiment of the present disclosure. In comparison to existing level set solvers, the SLBM 120 can identify anatomical structures with a parallel computational scheme, therefore leading to very fast computing performance over existing methods.

Figure 9:
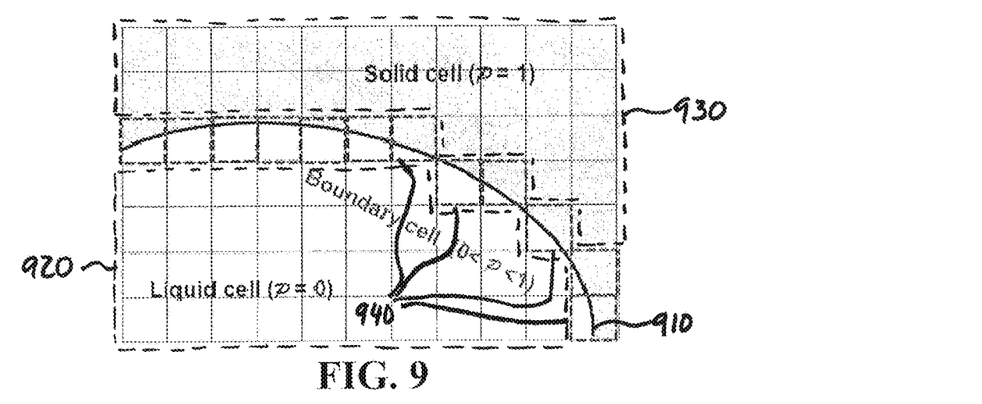
FIG. 9 is a representation of solid, fluid, and boundary cells, in accordance with an exemplary embodiment of the present disclosure.

Moreover, referring to FIG. 9, the SLBM-solved anatomical boundaries 910 are implicitly represented by the distance function to the boundaries at each computational grid cell. Such implicit geometric format makes it very easy to identify fluid cells 920, solid cells 930, and boundary cells 940 in the grid. Furthermore, it can immediately compute and dynamically update the volumetric fraction function, P, of each boundary cell for static and deformable arteries. Such a fast and direct computation of sub-grid volumetric fraction permits accurate patient-specific computational hemodynamics simulation by the VLBM 130, while in contrast, existing methods suffer from slow and complicated computation and unnecessary inaccuracy while explicitly creating boundary meshes and performing computational fluid dynamics simulations using different software tools. More geometric attributes, such as the boundary 810 normal, are also easily computed which are convenient to compute critical physical properties, such as wall shear stress.

Figure 11:
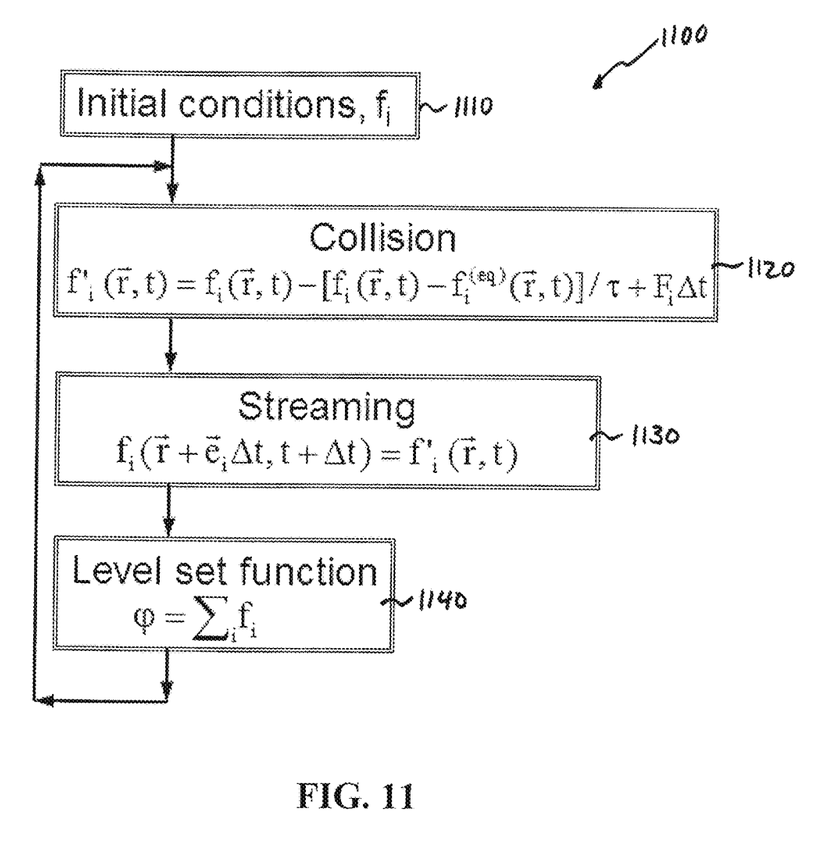
FIG. 11 is a flow chart of a simplified lattice Boltzmann method, in accordance with an exemplary embodiment of the present disclosure.

Referring now to FIG. 11, there is illustrated an exemplary method, generally designated as 1100, for implementing the SLBMs 120 and 150, in accordance with an exemplary embodiment of the present disclosure. The method 1100 is an exemplary implementation of the methods 120 and 150 illustrated in FIG. 1 and subroutine 320 of FIG. 3.

The method 1100 begins with receiving initial conditions $\varphi$, $f_i$, $f_i^{(eq)}$ at step 1110. Then, the method 1100 solves the following three equations to determine the velocity and pressure fields in the geometry:

$$f'_i(\vec{r},t) = f_i(\vec{r},t) - [f_i(\vec{r},t) - f_i^{eq}(\vec{r},t)]/\tau + F_i \Delta t \quad (2.)$$

$$f_i(\vec{r}+\vec{e}_i \Delta t, t+\Delta t) = f'_i(\vec{r},t) \quad (3.)$$

$$\varphi = \Sigma_i f_i \quad (4.)$$

The simplified lattice Boltzmann equations include: (a) collision, solved in accordance with equation 2 at step 1120, (b) streaming, solved in accordance with equation 3 at step 1130, and (c) updating distance field, calculated in accordance with equation 4 at step 1140.

The method 1100 is performed once as the SLBM 120 (subroutine 320). As the method 300 is executed to implement the framework 110, after the method 1100 is performed the first time (as the SLBM 120 or subroutine 320), the method 1100 is performed repeatedly in the SLBM for interface tracking 150, as illustrated in FIG. 1. Thus, during execution of the SLBM 150, after completion of the step 1140 in the method 1100, the method 1100 returns to the step 1120 and repeats steps 1120 through 1140. Steps 1120 through 1140 (and the SLBM 150) are repeated until the pulsation ends.

Step 1120 of collision is completely local in nature. Step 1130 of streaming requires information only from immediate neighboring nodes. Therefore, the method 1100 (SLBM 120 and 150 or subroutine 320, VLBM 130 or subroutine 330, and LSM 140 or subroutine 340) can be implemented with only local data access within workstation 210 and the computation at each node can be conducted concurrently. Such two features lead to parallel execution of the method 1100 for each node.

Further description of the SLBM 120 is provided in Appendices A, C, and D.

Volumetric Lattice Boltzmann Method

Figure 4:
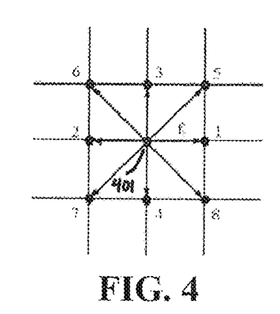
FIG. 4 is an example of a two-dimensional node-based model used in a traditional lattice Boltzmann method.
Figure 6:
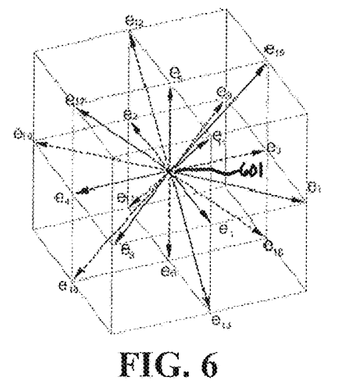
FIG. 6 is an example of a three-dimensional node-based model used in a traditional lattice Boltzmann method.
Figure 7:
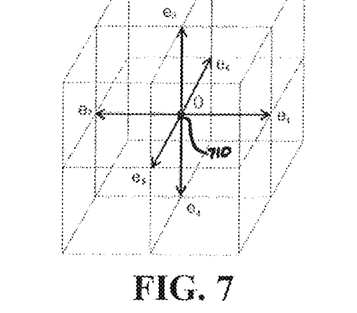
FIG. 7 is an example of a three-dimensional node-based model used in a simplified lattice Boltzmann method, in accordance with an exemplary embodiment of the present disclosure.

The traditional lattice Boltzmann method (LBM) is node based, dealing with the time evolution of particle density distribution functions, $f_i$ (i=0, 1, ..., b), at lattice node 401, as shown in FIG. 4 for 2-D meshes, and $e_i$ (i=0, 1, ..., b), as shown in FIG. 6 for 3-D meshes. Treatment of a curved boundary relies on point-wise interpolation or transformation into local curve-linear coordinate systems. Most node-based LBM schemes do not preserve exact conservations of mass and momentum and might fail to maintain the detailed balance among the particle density distribution functions resulting in numerical artifacts that may contaminate the fluid dynamics. Moreover, the realization of high-order interpolations involving nonlocal information is difficult and inefficient in general complex flows.

Figure 5:
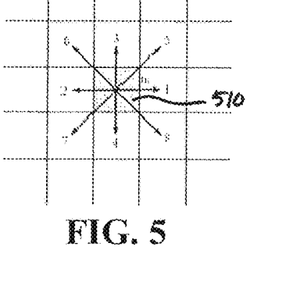
FIG. 5 is an example of a two-dimensional volume-based model used in a volumetric lattice Boltzmann method, in accordance with an exemplary embodiment of the present disclosure.

In accordance with an exemplary embodiment of the present disclosure, the VLBM 130 handles moving irregular boundaries. The VLBM 130 strictly satisfies mass conservation when the boundary passes over the flow domain. In the VLBM 130, similar to the concept of volume of fluid which has been used to track interfaces between two fluids, fluid particles are uniformly distributed in lattice cells, such as the lattice cell 510, as shown in FIG. 5, in accordance with an exemplary embodiment of the present disclosure. FIG. 5 illustrates a 2-D lattice and lattice cell 510.

In accordance with an exemplary embodiment of the present disclosure, the VLBM 130 solves volumetric lattice Boltzmann equations, which deal with time evolution of particle distribution functions, $n_i$ (i=0, 1, ..., b), characterized by a volumetric fraction function $P(\vec{r}, t)$. The volumetric fraction function, $P(\vec{r},t)$, is defined as the occupation of solid volume in the cell 510. Instead of constructing an advection equation to track moving interfaces in a volume of fluid, the volumetric fraction function, $P(\vec{r},t)$, in the VLBM 130 is introduced in the time evolution of the particle distribution functions, $n_i$ (i=0, 1, ..., b), by identifying three types of lattice cells in the simulation domain: solid, fluid, and boundary cells, as seen in FIG. 9.

Figure 12:
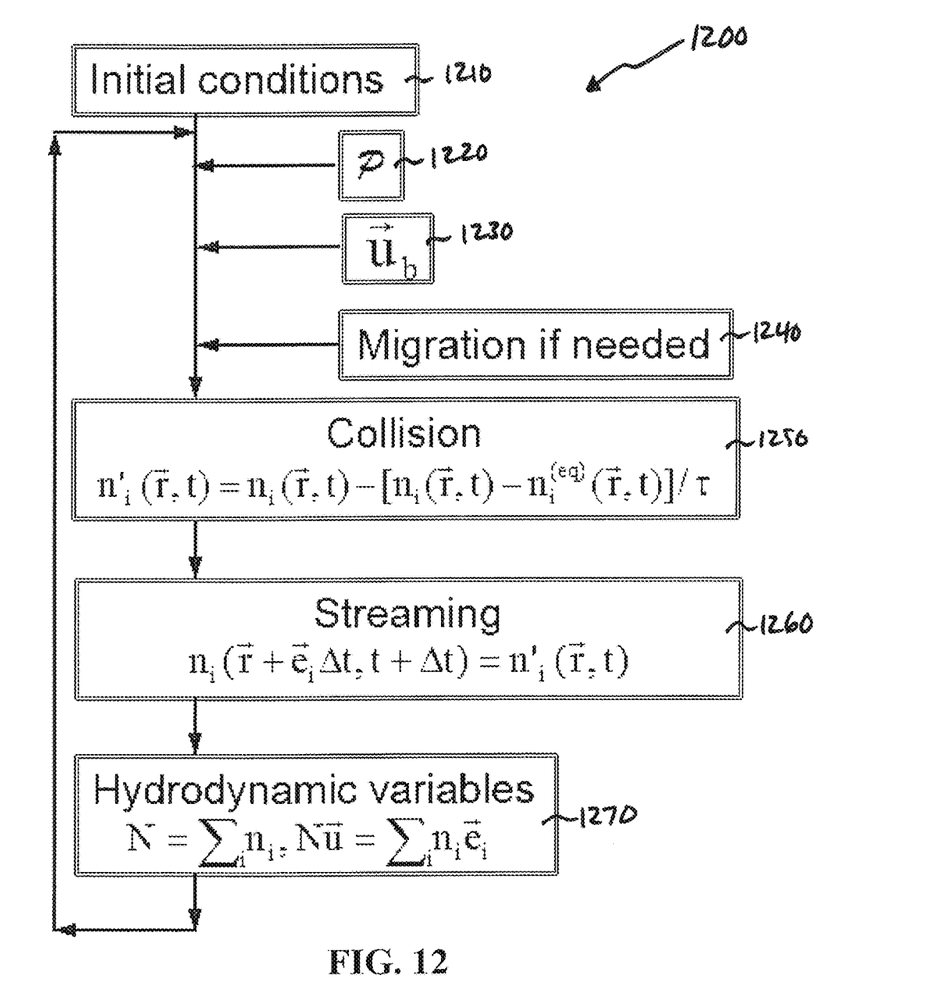
FIG. 12 is a flow chart of a volumetric lattice Boltzmann method, in accordance with an exemplary embodiment of the present disclosure.

Referring now to FIG. 12, there are illustrated exemplary steps of a method 1200 for implementing the VLBM 130 when the boundary is moving, in accordance with an exemplary embodiment of the present disclosure. The method 1200 is an exemplary implementation of the method 130 illustrated in FIG. 1 and subroutine 330 in FIG. 3. The method 1200 begins with receiving initial conditions at step 1210. P is received at step 1220, and $\vec{u}_b$ is received at step 1230. At step 1240, the boundary is moved if needed.

The method 1200 solves the following three equations to determine the velocity and pressure fields in the geometry:

$$n'_i(\vec{r},t) = n_i(\vec{r},t) - [n_i(\vec{r},t) - n_i^{eq}(\vec{r},t)]/\tau \quad (5.)$$

$$n_i(\vec{r}+\vec{e}_i \Delta t, t+\Delta t) = n'_i(\vec{r},t) \quad (6.)$$

$$N = \Sigma_i n_i, N\vec{u} = \Sigma_i n_i \vec{e}_i \quad (7.)$$

The volumetric lattice Boltzmann equations are formulated based on P including: (a) collisions, solved in accordance with equation (5), taking into account the received momentum from the moving boundary at step 1250, (b) streaming, solved in accordance with equation (6), accompanied with a volumetric bounce-back procedure in boundary cells at step 1260, and (c) boundary induced fluid migration, solved in accordance with equation (7), moving the residual fluid particles into the flow domain when the boundary swipes over a boundary cell toward a solid cell, as calculated in step 1240. The collision and streaming operations are more sophisticated than the node-based LBM, and fluid migration in the step 1240 is provided specifically to assure mass conservation. At step 1270, the hydrodynamic variables are updated in accordance with equation (7).

The relations between particle density distribution functions, $f_i$ (density $\rho$), in node-based LBM and the particle distribution functions, $n_i$ (particle number N), in VLBM are:

$$f_i = n_i/(1-P) \text{ and} \quad (8.)$$

$$\rho = N/(1-P), \quad (9.)$$

respectively.

In a pure fluid (P=0), the node-based and volume-based LBMs are identical.

Further description of the VLBM 130 is provided in Appendices B, C, and D.

Lattice Spring Model

Figure 10:
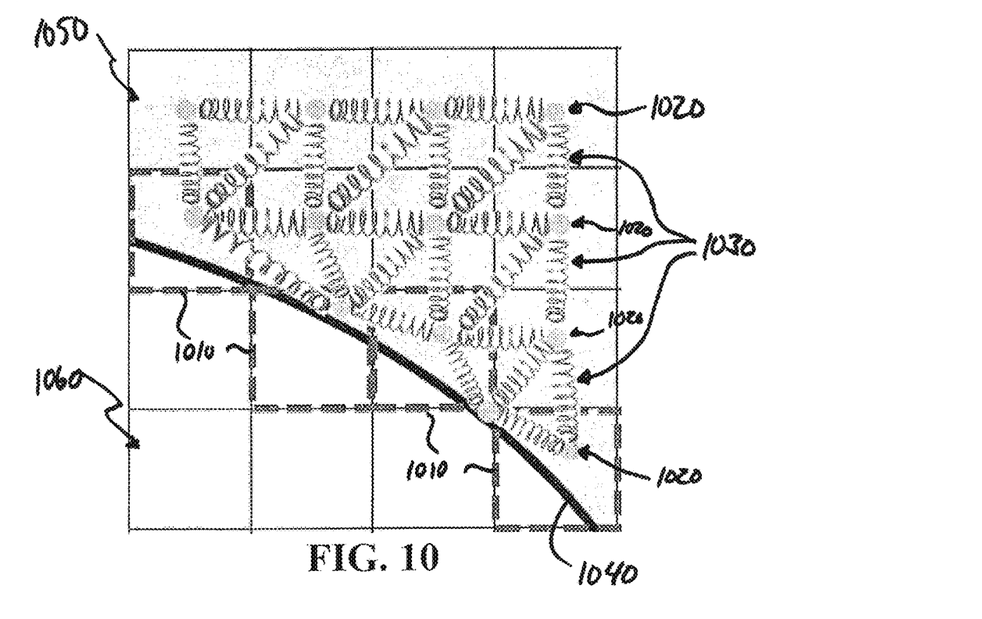
FIG. 10 illustrates a lattice spring model, in accordance with an exemplary embodiment of the present disclosure.

In the LSM 140, a 3-D lattice spring model for heterogeneous material is employed for the deformable structure, in accordance with an exemplary embodiment of the present disclosure. Referring to FIG. 10, in the lattice spring model, an elastic structure consists of solid particles 1020 initially sitting at the mass center of each boundary 1010 or solid cell 1050 and connected by a network of harmonic springs 1030. Initially each solid particle 1020, m, is labeled by $\vec{r}_{m0}$ with mass, $M_m$, and each spring is at its equilibrium length. When a spring 1030 is deformed, the elastic energy associated with the $m^{th}$ node 1020 is given by, $$U_m^s = 0.5 k_s \Sigma_n (\vec{r}_{mn} - \vec{r}_{0mn})^2, \quad (10.)$$

where $k_s$ is the spring constant and $$\vec{r}_{0mn} = \vec{r}_{m0} - \vec{r}_{n0}, \text{and} \quad (11.)$$

$$\vec{r}_{mn} = \vec{r}_m - \vec{r}_n \quad (12.)$$

are the lengths of the springs connecting two neighboring solid particles 1020, m and n, at equilibrium and deformed state respectively. The resulting spring force of the elastic energy is a two-body central force which allows either expansion or compression between two solid particles 1020.

For handling possible bending deformation, a three-body angular bond is introduced through an angular motion energy written as:

$$U_m^a = 0.5 k_a \Sigma_m \Sigma_{q,q \neq m} (\theta_{mnq} - \theta_{0mnq})^2, \quad (13.)$$

where $k_a$ is the angular coefficient, n and q are two nearest-neighboring solid particles of the $m^{th}$ solid particle 1020, $\theta_{mnq}$ is the angle between the bonding vectors, $\vec{r}_{mn}$ and $\vec{r}_{mq}$, and $\theta_{0mnq}$ is the corresponding equilibrium angle. The total elastic force, $\vec{F}_m$, on the $i^{th}$ solid particle 1020 can be computed from the gradient of the total energy as:

$$\vec{F}_m = -\nabla (U_m^s - U_m^a), \quad (14.)$$

As is understood by those skilled in the art with the benefit of the present disclosure, if more complicated deformation, such as twist, is involved, then a more complicated potential energy as a function of both distance and angle needs to be considered.

Two-way Coupling of Fluid and Structure Interface Update

The coupling of the fluid-structure interaction in boundary cells 1010 is implemented in the framework 110, in accordance with an exemplary embodiment of the present disclosure. On one side, the flow of the fluid cells 1060 imposes pressures and viscous stresses on the structure walls 1040. As seen in FIG. 10, in each boundary cell 1010, this force is taken to be equal to the rate of exchange in momentum that takes place as the particles of the fluid cells 1060 are bounced back at the interface 1040. Each LSM node 1020 receives a resultant force including the flow force and elastic forces summed over both boundary cells 1010 and neighboring LSM nodes 1020. To avoid noise at the interface, the force from flow is distributed over a certain cutoff distance.

On another side, when forced, the nodes 1020 of the solid cells 1050 move, thus generating elastic forces as described. By integrating Newton's equation of motion for solid particle m on which the net force is exerted, $$\vec{F}_m = M \frac{\partial^2 \vec{r}_m}{\partial t^2}, \quad (15.)$$

acceleration, velocity, and location of the solid particle m is updated through the velocity Verlet algorithm. The Verlet algorithm is described in Tuckerman, M., Berne, B. J., Martyna, G. J.: 'Reversible multiple time scale molecular-dynamics', J. Chem. Phys., 1992, 97, the contents of which are incorporated herein by reference.

At a boundary cell 1010, the fluid velocity equals the solid velocity. Again, to avoid velocity fluctuations, averaging and optimization within a certain neighboring area are desirable. The structure deformation desirable includes a track of the interface 1040, and the P value of each boundary cell 1010 is updated for the next time step.

The challenge is that ordering or connectivity of the solid particles 1020 and the topology of the real surface 1040 can be very complicated. A desirable interface tracking procedure should be able to easily handle complicated topology and to accurately represent the data set with certain smoothness. Three methods may be used based on the complexity of the application.

The first method is to reconstruct a triangulated interface using Delaunay triangulations and Voronoi diagrams, as described in Amenta, N. a. B., M.: 'Surface Reconstruction by Voronoi Filtering, Discrete and Comput.', Geometry 1999, 22, pp. 481-504, the contents of which are incorporated herein by reference. This method is straightforward but difficult to handle topological changes with explicit surfaces.

The second method is to generate a potential field for the evolution of a level-set function based on the solid particles' final position, as described in Zhao, H.-K., Osher, S., and Fedkiw, R.: 'Fast surface reconstruction using the level set method', in: 'Fast surface reconstruction using the level set method' (IEEE, 2001, edn.), pp. 194-201, the contents of which are incorporated herein by reference. The interface 1040 is then attracted to the boundary cell 1010 until it reaches a local equilibrium, where the potential field takes on a minimum value. Based on the new level set's distance field function, the P value of a boundary cell 1010 can be easily and accurately calculated by interpolation.

The third method is to treat solid particles 1020 as markers and use a particle level-set method to adjust the previous interface 1040, as described in Enright, D., Fedkiw, R., Ferziger, J., and Mitchell, I.: 'A Hybrid Particle Level Set Method for Improved Interface Capturing', Journal of Computational Physics, 2002, 183, pp. 83-116, the contents of which are incorporated herein by reference. These particles 1020 are initially given a fixed radius of influence based on their distance from the initial interface 1040 location. When a particle's 1020 position is changed, the particle's 1020 sphere of influence is used to update the interface 1040.

The second and third methods are more sophisticated than the first method but can be solved by SLBM 120, 150 efficiently.

Appendix A describes VLBM 130 and GPU parallelization in further detail.

The framework 110 has (1) programming simplicity without compromising physical accuracy; (2) easy modeling of interfacial dynamic behavior of deformable arteries and fluids; (3) fast computational performance enabled by GPU acceleration which is local and low-cost. Therefore the framework 110 leads to patient-specific hemodynamics simulation and analysis within a clinically acceptable time. After being integrated with clinical MRI or CT imagers 102, this unified and GPU-accelerated framework 110 will enable access of medical practitioners to the quantitative hemodynamics and wall shear stress (WSS) information in diseased arteries simultaneously with CT/MRI imaging, which has not been made possible in existing approaches. It is also useful for massive secondary data analysis of existing medical images. The framework 110 can promote deeper understanding of vascular diseases and lay the groundwork for future improvements in patient care and clinical decision making.

Although it is described that the architecture 100 is for calculating blood flow and blood-artery/plaque interaction, it is to be understood that the architecture is not so limited. Other applications of the architecture 100 are contemplated for calculating the flow of any fluid in an anatomical vessel, e.g., urine flow, air flow, blood flow in a heart ventricle, etc. Furthermore, the architecture 100 is not limited to calculating fluid flow in humans. It may be used in any living animal or in any vessel in which fluid flows.

These and other advantages of the present disclosure will be apparent to those skilled in the art from the foregoing specification. Accordingly, it is to be recognized by those skilled in the art that changes or modifications may be made to the above-described embodiments without departing from the broad inventive concepts of the disclosure. It is to be understood that this disclosure is not limited to the particular embodiments described herein, but is intended to include all changes and modifications that are within the scope and spirit of the disclosure.

What is claimed is:

1. A method of non-invasively quantifying in vivo blood flow and flow-artery interaction in an artery, comprising:
   receiving image data of anatomical features of the artery;
   processing the image data on a GPU parallel-computation framework employing mesoscale models; and
   causing display of information representing the flow-artery interaction;
   wherein processing comprises
   using a simplified lattice Boltzmann method ("SLBM") to model anatomical segmentation of the artery,
   using a volumetric lattice Boltzmann method ("VLBM") to model fluid dynamics of the flow-artery interaction,
   using a lattice spring method ("LSM") to model structure mechanics of the flow-artery interaction, and
   using the SLBM to model interface tracking of the flow-artery interaction.

2. The method of claim 1 wherein receiving image data comprises receiving image data from at least one of a CT scanner, an MRI imager and an ultrasound Doppler imager.

3. The method of claim 1 wherein displaying information representing the flow-artery interaction comprises displaying at least one of a 3D blood flow velocity map and a wall shear stress map.

4. The method of claim 1 wherein the GPU parallel-computation framework is a GPU-equipped workstation.

5. The method of claim 1 wherein using an SLBM includes performing a collision calculation, performing a streaming calculation and updating a distance function.

6. The method of claim 5 wherein performing a collision calculation comprises solving $f'_i(\vec{r},t)=f_i(\vec{r},t)-[f_i(\vec{r},t)-f_i^{eq}(\vec{r},t)]/\tau+F_i\Delta t$.

7. The method of claim 5 wherein performing a streaming calculation comprises solving $f_i(\vec{r}+\vec{e}_i\Delta t,t+\Delta t)=f'_i(\vec{r},t)$.

8. The method of claim 5 wherein updating a distance function comprises calculating $\varphi=\Sigma_i f_i$.

9. The method of claim 1 wherein using a VLBM includes performing a collision calculation and performing a streaming calculation.

10. The method of claim 9 wherein performing a collision calculation comprises solving $n'_i(\vec{r},t)=n_i(\vec{r},t)-[n_i(\vec{r},t)-n_i^{eq}(\vec{r},t)]/\tau$.

11. The method of claim 9 wherein performing a streaming calculation comprises solving
$n_i(\vec{r}+\vec{e}_i\Delta t,t+\Delta t)=n'_i(\vec{r},t)$.

12. The method of claim 9 wherein using a VLBM includes determining boundary induced fluid migration by solving $N=\Sigma_i n_i$, $N\vec{u}=\Sigma_i n_i \vec{e}_i$.

* * * * *